United States Patent [19]

Reese et al.

[11] 4,005,189
[45] Jan. 25, 1977

[54] PROCESS OF SUPPRESSING ODORS EMPLOYING DEODORANTS CONTAINING ESTERS OF ALIPHATIC HYDROXYCARBOXYLIC ACIDS

[75] Inventors: Günter Reese, Dusseldorf-Holthausen; Rainer Osberghaüs, Dusseldorf-Urdenbach, both of Germany

[73] Assignee: Henkel & Cie G.m.b.H., Dusseldorf-Holthausen, Germany

[22] Filed: Apr. 2, 1975

[21] Appl. No.: 564,554

[30] Foreign Application Priority Data

Apr. 16, 1974 Germany ............................ 2418362

[52] U.S. Cl. ........................... 424/47; 424/DIG. 5; 424/65; 424/357
[51] Int. Cl.² .......................................... A61K 7/32
[58] Field of Search ............................ 424/47, 313
[56] References Cited
UNITED STATES PATENTS

| 3,124,506 | 3/1964 | Holman ........................... 424/65 X |
| 3,833,720 | 9/1974 | Crotty et al. ........................ 424/47 |

FOREIGN PATENTS OR APPLICATIONS 2,225,313  12/1972  Germany ............................ 424/47

OTHER PUBLICATIONS

Neurath et al. 1968, vol. 69, p. 1832j, Chem. Abs.
Bomar, Chem. Abs., 1968, vol. 69, p. 67994.
Webb et al. Chem. Abs; 1968, vol. 68, p. 769i5b.
Capouillez et al., Chem. Abs., vol. 70, 1969 p. 6519t.

*Primary Examiner*—Dale R. Ore
*Attorney, Agent, or Firm*—Hammond & Littell

[57] ABSTRACT

A process of suppressing body odors comprising applying a substantially anhydrous cosmetic preparation for supressing body odor containing as a deodorant an ester of an aliphatic mono- or di-hydroxycarboxylic acid or an aliphatic mono- or di-hydroxy-dicarboxylic acid having from 2 to 4 carbon atoms with an aliphatic alcohol having from 1 to 6 carbon atoms, or an alicyclic alcohol having 5 to 6 carbon atoms.

5 Claims, No Drawings

PROCESS OF SUPPRESSING ODORS EMPLOYING DEODORANTS CONTAINING ESTERS OF ALIPHATIC HYDROXYCARBOXYLIC ACIDS

It is known that the troublesome odor which accompanies human perspiration is caused by the bacterial decomposition of the initially odorless perspiration. There have therefore been numerous suggestions for ways of overcoming this difficulty, but no universally satisfactory solution has hitherto been found. Basically two methods of solving this problem have been proposed. Firstly, the use of antimicrobial compounds for killing the bacterial skin flora which cause the decomposition of the perspiration, and secondly, the use of compounds which prevent the secretion of perspiration. In addition to the above agents, compositions which have a purely absorptive action and which mask the odor are of lesser importance. In contrast to the anti-perspirants, the cosmetic compositions which have a deodorizing action without exception contain antimicrobial substances.

The following are examples of substances which have been proposed and, in some cases, used in deodorant compositions: phenol derivatives with and without halogen substituents, organic mercury compounds, quaternary ammonium compounds and derivatives of amino acids having a disinfectant action. Even though the risk of skin irritations is not as great when deodorants are used as when anti-perspirants are used; nevertheless, various degrees of incompatibility, sensitivity with respect to light and toxic side effects do occur periodically when deodorants containing antimicrobial agents are used constantly. Furthermore, the majority of these products are not odorless and many have a slight phenolic odor. Attempts have therefore also been made to produce cosmetic compositions which are very good deodorants, are neutral with respect to odor and are largely free from side effects.

It is an object of the present invention to provide a process of suppressing body odors comprising applying a substantially anhydrous cosmetic preparation for suppressing body odor containing as a deodorant an ester of an aliphatic mono- or di-hydroxycarboxylic acid or an aliphatic mono- or di-hydroxy-dicarboxylic acid having from 2 to 4 carbon atoms with an aliphatic alcohol having from 1 to 6 carbon atoms, or an alicyclic alcohol having 5 to 6 carbon atoms.

Another object of the invention is to provide a substantially anhydrous cosmetic composition for suppressing body odor containing, as a deodorant, from about 1% to 25% by weight of at least one of the above esters.

This and further objects of the present invention will become apparent as the description thereof proceeds.

The invention relates to cosmetic preparations for suppressing body odor which contain a deodorant and the process of suppressing body odor by applying the same to the body.

It has now been discovered that the utilization of esters of aliphatic mono- and di-hydroxycarboxylic acids and aliphatic mono- and di-hydroxy-dicarboxylic acids having 2 to 4 carbon atoms in the molecule with aliphatic alcohols having 1 to 6 carbon atoms in the molecule or alicyclic alcohols having 5 to 6 carbon atoms in the molecule, as deodorants in substantially anhydrous cosmetic preparations for the suppression of body odor substantially fulfills the above-mentioned requirements.

More particularly, the present invention provides a process for suppressing body odor in a warm-blooded animal comprising applying topically to said warm-blooded animal an effective deodorizing amount of a substantially anhydrous cosmetic preparation containing from 1% to 25% by weight based upon the total weight of at least one ester of an aliphatic acid having from 2 to 4 carbon atoms selected from the group consisting of hydroxyalkanoic acids, dihydroxyalkanoic acids, hydroxyalkanedioic acids and dihydroxyalkanedioic acids with an alcohol selected from the group consisting of alkanols having from 1 to 6 carbon atoms, cycloalkanols having from 5 to 6 carbon atoms and alkanepolyols having 2 to 6 carbon atoms and 2 to 6 hydroxy groups; and the remainder of inert cosmetic ingredients.

The fact that the cosmetic preparations used according to the process of the invention are substantially anhydrous is desirable for reasons of stability during storage of such products. However, water contents of up to 5% can be tolerated in special cases, depending on the ester used and the requirements with respect to stability. Such preparations containing a little water are still regarded as substantially anhydrous in accordance with the present invention.

The esters of the aliphatic mono- or di-hydroxycarboxylic acids and aliphatic mono- or di- hydroxy-dicarboxylic acids having 2 to 4 carbon atoms in the molecule, which esters are to be used in accordance with the invention, can be produced in a known manner by azeotropic esterification of the acids with the appropriate alcohol.

Suitable examples of acids are aliphatic mono- and dihydroxy carboxylic acids, and mono- and di-hydroxy-dicarboxylic acids having 2 to 4 carbon atoms, for example, monohydroxyalkanoic acids having 2 to 4 carbon atoms such as glycolic acid, lactic acid, β-hydroxypropionic acid and β-hydroxybutyric acid, monohydroxy alkanedioic acids having 3 to 4 carbon atoms such as tartronic acid and malic acid, dihydroxy alkanoic acids having 3 to 4 carbon atoms such as glyceric acid, and dihydroxy alkanedioic acids having 3 to 4 carbon atoms such as tartaric acid.

Examples of suitable esterifying aliphatic or alicyclic alcohols having 1 to 6 carbon atoms include alkanols having 1 to 6 carbon atoms such as methanol, ethanol, propanol, isopropanol, butanol-1, butanol-2, 2-methylpropanol-1, 2-methylpropanol-2, 2-methylbutanol-1, 2 methylbutanol-4 and n-hexylalcohol. Also included are alkanediols having 2 to 6 carbon atoms such as ethyleneglycol, propyleneglycol, trimethyleneglycol and hexamethyleneglycol, and alkane triols having 3 to 6 carbon atoms such as glycerine, alkanetetrols having 4 to 6 carbon atoms such as erythritol, and alkanehexols having 4 to 6 carbon atoms such as sorbitol, and cycloalkanols having 5 to 6 carbon atoms such as cyclohexanol.

Among the esters of the aliphatic hydroxycarboxylic acids to be used in accordance with the invention, the respective full esters are preferred, both with respect to their deodorizing activity and their suitability for use, especially the full esters from aliphatic monohydric alcohols with 1 to 6 carbon atoms in the molecule.

Accordingly, examples of esters of aliphatic hydroxycarboxylic acids, which can be used in accordance with the invention are cyclohexyl glycolate, hydroxyethyl glycolate, glyceryl monoglycolate, 2-hydroxypropyl lactate, sorbityl lactate, methyl hydroxybutyrate, isopropyl hydroxybutyrate, hexyl hydroxybutyrate, erythrityl hydroxybutyrate, cyclohexyl glycerinate, hydroxypropyl glycerinate, monomethyl tartronate, monoethyl tartronate, monopropyl tartronate, monobutyl tartronate, monoamyl tartronate, monohexyl tartronate, hydroxyethyl tartronate, glyceryl monotartronate, monomethyl malate, monoethyl malate, monoisopropyl malate, monoisobutyl malate, mono-tert.-butyl malate, monoamyl malate, cyclohexyl malate, mono-2-hydroxypropyl malate, mono-hydroxyhexyl malate, monomethyl tartarate, monoethyl tartarate, monopropyl tartarate, monoisopropyl tartarate, monobutyl tartarate, monoamyl tartarate, monohexyl tartarate, mono-hydroxyethyl tartarate, monoerythrityl tartarate and mono-sorbityl tartarate. Preferred esters are methyl glycolate, ethyl glycolate, propyl glycolate, isopropyl glycolate, butyl glycolate, isobutyl glycolate, tert.-butyl glycolate, amyl glycolate, hexyl glycolate, methyl lactate, ethyl lactate, propyl lactate, isopropyl lactate, butyl lactate, tert.-butyl lactate, hexyl lactate, methyl β-hydroxypropionate, ethyl β-hydroxypropionate, isopropyl β-hydroxypropionate, butyl β-hydroxypropionate, amyl β-hydroxypropionate, methyl glycerinate, ethyl glycerinate, propyl glycerinate, butyl glycerinate, hexyl glycerinate, dimethyl tartronate, diethyl tartronate, diisopropyl tartronate, dibutyl tartronate, diamyl tartronate, dimethyl malate, diethyl malate, dipropyl malate, diisopropyl malate, dibutyl malate, dihexyl malate, dimethyl tartarate, diethyl tartarate, dipropyl tartarate, diisopropyl tartarate, dibutyl tartarate, di-tert.- butyl tartarate, diamyl tartarate and dihexyl tartarate.

The esters of the aliphatic hydroxycarboxylic acids with aliphatic or alicyclic alcohols for use in the cosmetic preparations of the invention, can be incorporated into all anhydrous preparations or substantially anhydrous preparations with a low water content, which are generally used as deodorants, and they include powders, sticks, roll-ons and sprays. The deodorant spray is the preferred embodiment of use. Incorporation is effected in a known manner, simply by stirring in or dissolving in the other constituents of the preparation, namely inert cosmetic ingredients, such as solvents, waxes, fatty substances, polyglycols and powder bases. The amounts of esters of aliphatic hydroxycarboxylic acids having 2 to 4 carbon atoms in the molecule, with aliphatic or alicyclic alcohols having 1 to 6 carbon atoms in the molecule, in the cosmetic composition or preparation of the invention with a deodorizing activity are from 1% to 25% by weight, preferably 5% to 15% by weight, based upon the total weight of the preparation.

Enough of this preparation is applied topically to a warm-blooded animal to constitute an effective deodorizing amount for the suppression of body odor.

The esters of aliphatic hydroxycarboxylic acids are preferably used in the deodorizing cosmetic preparations as the sole deodorant although a combination with other deodorizing substances is possible.

It is already known from the German Offenlegungsschrift (DOS) No. 2,225,313 that ethyl lactate can be used for the treatment of acne or Pityriasis oleosa capitis, but it could not be concluded therefrom that this product constitutes an effective deodorant. Furthermore, the use of malic acid esters in beauty creams and shaving creams is known from the German Offenlegungsshrift (DOS) No. 1,792,353. Esters having a lipophilic and hydrophobic alcohol component are expressly dealt with in this DOS. However, such higher molecular esters do not have a deodorizing action. Moreover, the free hydroxycarboxylic acids or their salts, on which the esters to be used in accordance with the invention are based, have already been described as additions for cosmetic preparations. Here again, the free hydroxycarboxylic acids or their salts do not possess any deodorizing action.

It was therefore extremely surprising that the esters of aliphatic hydroxycarboxylic acids, having 2 to 4 carbon atoms in the molecule, with aliphatic or alicyclic alcohols having 1 to 6 carbon atoms, especially the corresponding full esters with aliphatic, monohydric alcohols having 1 to 6 carbon atoms in the molecule, are marked by exceptional deodorizing effectiveness.

The following examples are merely illustrative of the present invention without being deemed limitative in any manner thereof.

EXAMPLES

Cosmetic preparations of the invention having a deodorizing activity can be produced in accordance with the basic recipes given hereinafter. All parts are by weight unless otherwise indicated.

EXAMPLE 1

| Deodorant stick | Parts |
| --- | --- |
| 2-octyldodecanol | 26.0 |
| Cetyl/stearyl alcohol | 3.0 |
| Sodium stearate | 8.0 |
| Coconut fatty acid monoethanol amide | 3.0 |
| Paraffin oil | 2.0 |
| Propylene glycol | 2.0 |
| Ethanol | 48.5 |
| Dibutyl tartarate | 7.5 |

EXAMPLE 2

| Deodorant powder | Parts |
| --- | --- |
| Rice starch | 10.0 |
| Magnesium carbonate | 2.0 |
| Zinc oxide | 2.0 |
| Extra fine talcum | 76.0 |
| Dihexyl malate | 10.0 |

EXAMPLE 3

| Deodorant spray | Parts |
| --- | --- |
| Butyl lactate | 10.0 |
| Ethanol | 26.0 |
| Isopropanol | 2.8 |
| Propylene glycol | 1.2 |
| (dichlorodifluoromethane/dichlorotetrafluoroethane 60:40) | 60.0 |

EXAMPLE 4

| Deodorant spray | Parts |
| --- | --- |
| Diethyl tartarate | 5.0 |
| Ethanol | 10.0 |
| Isopropanol | 18.0 |
| Isopropyl myristate | 2.0 |
| Propellant gas (Frigen 12/114) (dichlorodifluoromethane/dichlorotetrafluoroethane 60:40) | 65.0 |

EXAMPLE 5

| Deodorant spray | Parts |
| --- | --- |
| Diethyl malate | 7.0 |
| Caprylic/capric acid triglyceride | 4.0 |
| Propellant gas (Frigen 12/114) (dichlorodifluoromethane/dichlorofluoroethane 60:40) | 89.0 |

EXAMPLE 6

| Deodorant spray -continued | Parts |
|---|---|
| Butyl glycolate | 15.0 |
| Propylene glycol | 1.5 |
| Isopropyl stearate | 1.5 |
| Propellant gas (Frigen 12/114) (dichlorodifluoromethane/dichlorofluoroethane 60:40) | 82.0 |

EXAMPLE 7

| Deodorant spray | Parts |
|---|---|
| Diisopropyl tartronate | 10.0 |
| Propylene glycol | 2.0 |
| Isopropyl myristate | 2.0 |
| Ethanol | 11.0 |
| Propellant gas (Frigen 11/12) (trichlorofluoromethane/dichlorodifluoromethane 50:50) | 75.0 |

EXAMPLE 8

| Deodorant spray | Parts |
|---|---|
| Cyclohexyl glycerinate | 10.0 |
| Ethanol | 27.0 |
| Isopropyl myristate | 3.0 |
| Propellant gas (Frigen 12) (dichlorodifluoromethane) | 60.0 |

EXAMPLE 9

| Deodorant spray | Parts |
|---|---|
| Diisopropyl malate | 5.0 |
| Ethanol | 26.0 |
| Isopropanol | 7.0 |
| Propylene glycol | 2.0 |
| Propellant gas (Frigen 12/114) (dichlorodifluoromethane/dichlorodifluoroethane 60:40) | 60.0 |

EXAMPLE 10

| Deodorant spray | Parts |
|---|---|
| Dimethyl tartrate | 10.0 |
| Isopropyl myristate | 3.0 |
| Ethanol | 17.0 |
| Isopropanol | 10.0 |
| Propellant gas (Frigen 11/12) (trichlorofluoromethane/dichlorodifluoromethane 50:50) | 60.0 |

| Deodorant spray A (Invention) | Parts |
|---|---|
| Ethyl lactate | 5.0 |
| Isopropanol | 4.0 |
| Ethanol | 31.0 |
| Propellant gas (Frigen 12) (dichlorodifluoromethane) | 60.0 |

| Comparative spray B | Parts |
|---|---|
| Lactic acid | 5.0 |
| Isopropanol | 4.0 |
| Ethanol | 31.0 |
| Propellant gas (Frigen 12) (dichlorodifluoromethane) | 60.0 |

A test group consisting of 15 female and 15 male participants first of all used a soap F, which was free of antimicrobial agents, for a period of 5 days, with no deodorants or antiperspirants being used. Subsequently each participant was given a T-shirt and was instructed to treat one shoulder with the deodorant spray A on the morning of the sixth day after washing with soap F, and, for purposes of comparison, not to treat the other shoulder, one half of the group treating the left shoulder and the other half treating the right shoulder. The formation of odor was estimated by the test persons themselves and also by two cosmetic experts, by smelling the T-shirts after 8 hours and 24 hours. Subsequently, the test persons used soap F alone for a week. The test was then repeated, the hitherto untreated shoulder being treated with the deodorant spray and the other shoulder serving for comparison.

In both tests it was determined by all the persons taking part therein that the deodorant spray A prevented odor very well.

The test was repeated in a completely analogous procedure with the same test group, except that the only difference was that in each case comparative spray B was used instead of deodorant spray A. In this test, none of the participants could ascertain any significant reduction in odor.

EXAMPLE 12

The tests carried out using the deodorant spray A were repeated in a completely analogous procedure with the same test group, except that the only difference was that the deodorant spray C having the following composition was used instead of deodorant spray A.

| Deodorant spray C (Invention) | Parts |
|---|---|
| Diethyl malate | 10 |
| Ethanol | 30 |
| Propellant gas (Frigen 12) (dichlorodifluoromethane) | 60 |

In both tests a very good capacity for suppressing odor was again determined for deodorant spray C by all test participants.

EXAMPLE 13 (Comparative)

The test carried out using deodorant spray C was repeated in a completely analogous procedure with the same test group, except that di-(2-phenylethyl) malate was used as the deodorant in the spray in place of the deodorant diethyl malate of spray C, in accordance with Example 1 of the German Offenlegungsschrift (DOS) No. 1,792,353. The comparative spray D had the following composition:

| Comparative spray D | Parts |
|---|---|
| Di-(2-phenylethyl) malate | 10 |
| Ethanol | 30 |
| Propellant gas (Frigen 12) (dichlorodifluoromethane) | 60 |

In this comparative test none of the participants could ascertain any significant reduction in odor.

Although the present invention has been disclosed in connection with a few preferred embodiments thereof, variations and modifications may be resorted to by those skilled in the art without departing from the principles of the new invention. All of these variations and modifications are considered to be within the true spirit and scope of the present invention as disclosed in the foregoing description and defined by the appended claims.

We claim:

1. A process for suppressing body odor in a warmblooded animal comprising applying topically to said warmblooded animal an effective deodorizing amount of a substantially anhydrous cosmetic preparation containing from 1% to 25% by weight based upon the total weight of at least one ester of an aliphatic acid having from 2 to 4 carbon atoms selected from the group consisting of a hydroxyalkanoic acid, a dihydroxyalkanoic acid, a hydroxyalkanedioic acid and a dihydroxyalkanedioic acid with an alcohol selected from the group consisting of an alkanol having from 1 to 6 carbon atoms, a cycloalkanol having from 5 to 6 carbon atoms and an alkanepolyol having 2 to 6 carbon atoms and 2 to 6 hydroxy groups; and the remainder of inert cosmetic ingredients.

2. The process of claim 1, wherein said ester is a full ester.

3. The process of claim 1, wherein said preparation contains from 5 to 15% by weight, based upon the total weight of said ester.

4. The process of claim 1, wherein said preparation contains a propellant gas and is applied topically by spraying as a deodorant spray.

5. A process for suppressing body odor in a warmblooded animal comprising applying topically to said warmblooded animal an effective deodorizing amount of at least one ester of an aliphatic acid having from 2 to 4 carbon atoms selected from the group consisting of a hydroxyalkanoic acid, a dihydroxyalkanoic acid, a hydroxyalkanedioic acid and dihydroxyalkanedioic acid with an alcohol selected from the group consisting of an alkanol having from 1 to 6 carbon atoms, a cycloalkanol having from 5 to 6 carbon atoms and an alkanepolyol having 2 to 6 carbon atoms and 2 to 6 hydroxy groups.

* * * * *